(12) United States Patent
Ballard (10) Patent No.: US 6,777,623 B2
(45) Date of Patent: Aug. 17, 2004

(54) SYSTEM AND METHOD OF TRACKING SURGICAL SPONGES

(76) Inventor: M. Daniel Ballard, 4900 W. William Cannon, Austin, TX (US) 78749

( * ) Notice: Subject to any disclaimer, the term of this patent is extended or adjusted under 35 U.S.C. 154(b) by 153 days.

(21) Appl. No.: 10/124,534

(22) Filed: Apr. 17, 2002

(65) Prior Publication Data

US 2003/0196837 A1 Oct. 23, 2003

(51) Int. Cl.[7] .......................... A61F 13/16; G01G 19/40
(52) U.S. Cl. ............................... 177/25.13; 177/25.17; 177/25.19; 177/245; 235/385; 340/505; 604/317; 604/584; 600/573; 600/584; 128/897; 128/898; 128/899; 705/28
(58) Field of Search ........................... 177/25.11–25.19, 177/245; 600/573, 584; 604/317, 362; 128/897–899; 340/505; 235/385; 705/28

(56) References Cited

U.S. PATENT DOCUMENTS

| | | | | |
|---|---|---|---|---|
| 3,698,393 A | * | 10/1972 | Stone | 604/362 |
| 3,756,241 A | * | 9/1973 | Patience | 604/362 |
| 3,834,390 A | * | 9/1974 | Hirsch | 604/362 |
| 3,948,390 A | | 4/1976 | Ferreri | |
| 4,157,738 A | * | 6/1979 | Nishiguchi et al. | 177/1 |
| 4,193,405 A | * | 3/1980 | Abels | 604/362 |
| 4,205,680 A | * | 6/1980 | Marshall | 604/362 |
| 4,295,537 A | * | 10/1981 | McAvinn et al. | 177/15 |
| 4,422,548 A | * | 12/1983 | Cheesman et al. | 206/370 |
| 4,477,256 A | * | 10/1984 | Hirsch | 604/362 |
| 4,478,332 A | | 10/1984 | Wiestmiller | |
| 4,784,267 A | | 11/1988 | Gessier et al. | |
| 4,832,198 A | | 5/1989 | Alikhan | |
| 4,922,922 A | * | 5/1990 | Pollock et al. | 600/573 |
| 4,925,048 A | | 5/1990 | Noack | |
| 4,935,019 A | * | 6/1990 | Papp, Jr. | 604/362 |
| 4,938,901 A | * | 7/1990 | Groitzsch et al. | 264/477 |
| 5,041,103 A | * | 8/1991 | Rupinskas | 604/362 |
| 5,057,095 A | | 10/1991 | Fabian | |
| 5,629,498 A | | 5/1997 | Pollock et al. | |
| 5,664,582 A | | 9/1997 | Szymaitis | |
| 5,923,001 A | | 7/1999 | Morris et al. | |
| 6,354,493 B1 | * | 3/2002 | Mon | 235/380 |
| 6,388,569 B1 | * | 5/2002 | Engellenner | 340/505 |

OTHER PUBLICATIONS

Kaiser et al., The Retained Surgical Sponge, Annuls of Surgery, v. 224, No. 1, pp. 79–84, (1996).

* cited by examiner

Primary Examiner—Randy W. Gibson
(74) Attorney, Agent, or Firm—Greg K. Goshorn; Hulsey Grether + Fortkort LLP (57) ABSTRACT

The apparatus and method is provided that employs a "radiopaque" object to count and account for surgical sponges in an operating room. A radiopaque object is embedded in surgical sponges so that a scanning device can detect and count a large number of the sponges within a container. The container is designed to minimize contact with the sponges by humans. In addition, a surgical team can insure that no surgical sponge is left in a patient without performing the messy and time-consuming job of individually counting sponges as they are entered and disposed of from the surgical site.

35 Claims, 8 Drawing Sheets

SYSTEM AND METHOD OF TRACKING SURGICAL SPONGES

BACKGROUND

1. Technical Field

The invention relates generally to an apparatus and method for tracking surgical supplies and, more specifically, to counting and accounting for all disposable surgical sponges used in a surgical procedure.

2. Related Art

During surgical procedures, absorbent sponges are employed to soak up blood and other fluids in and around the incision site. In a study entitled "The Retained Surgical Sponge" (Kaiser, et al., *The Retained Surgical Sponge*, Annals of Surgery, vol. 224, No. 1, pp. 79–84), surgical sponges were found to have been left inside a patient following surgery in 67 of 9729 (0.7%) medical malpractice insurance claims reviewed. In those 67 cases, the mistake was attributed to an incorrect sponge count in seventy-six percent (76%) of the cases studied, and attributed to the fact that no count was performed in ten percent (10%) of the cases studied. Typically, a sponge left inside a patient is presumed to indicate that substandard and negligent care has taken place. Clearly, it is in both a patient's and the health care providers' best interest to account for every surgical sponge used in any particular surgical procedure.

As explained in U.S. Pat. No. 5,923,001 entitled Automatic Surgical Sponge Counter and Blood Loss Determination System, sponge counts are an essential step in operating room procedure. Sponge counts are a difficult procedure for a number of reasons. For example, the handling of soiled sponges carries the risk of transmission of blood borne diseases such as hepatitis B virus (HBV) and human immunodeficiency virus (HIV). Therefore, used sponges are handled with gloves and/or instruments and the handling is kept to a minimum. Another difficulty is that the counting process is typically tedious, time-consuming and frustrating.

Sponge counts are typically performed multiple times during a surgical procedure, both at the beginning and throughout the procedure as sponges are added, before closure of a deep incision or body cavity, and during personnel breaks and shift changes. Thus, within all the activity of an operating room, maintaining an accurate sponge is difficult, as evidenced by the error rate mentioned in the Keiter article, quoted above.

There do exist products to make the procedure both simpler and more reliable. For example, various systems facilitate the hand-counting of surgical sponges by arranging the sponges into visually inspectible groups or arrangements (see U.S. Pat. Nos. 3,948,390, 4,364,490, 4,784,267, 4,832,198, 4,925,048 and 5,658,077). These systems are problematic because surgeons and anesthesiologists often determine blood loss by means of visual inspection or a manual weighing of soiled sponges and so soiled sponges are typically kept in one area of an operating room during a surgical procedure, thus creating the possibility that groupings are co-mingled or counted twice. In addition, operating room workers are often too rushed, fatigued and/or distracted to accurately count a large number of soiled sponges lumped together in one or more groups. This method also depends upon the accuracy of an initial count and, if the number of sponges in the original package is mislabeled by the manufacturer, then a missing sponge may be missed during a final count.

A second solution to the surgical sponge tracking problem is the inclusion of a radiopaque thread in the sponges. A radiopaque thread can be identified and located if a sponge is accidentally left inside a patient. Thus, if a patient develops a problem such as an abscess, a bowel obstruction, or internal pain at any time following an operation, a sponge that has been left in the body can be detected by x-ray. Companies that market sponges with radiopaque threads include Johnson & Johnson, Inc. of New Brunswick, N.J., Medline Industries of Mundelein, Ill. and the Kendall Company of Mansfield, Mass.

A third solution to the sponge problem is the inclusion of a radio frequency identification (RFID) tag in each sponge (see U.S. Pat. No. 5,923,001). The RFID tag enables a patient to be scanned to detect the presence of a sponge within a body cavity, but RFID tags may cost several times what a typical surgical sponge costs and are also bulky, impairing the usefulness of the sponge.

Another solution to the sponge problem is a device that counts sponges as they are dropped, one-by-one, into an opening, or "entry gate," of the device (see U.S. Pat. No. 5,629,498). This solution is restricted by the accuracy of the original count and the precision of operating room assistants as they separate sponges from one another and drop them into the entry gate, one-by-one.

A final, exemplary solution involves attaching a magnetic resonance device, or marker tag, to each sponge, which are then scanned by appropriate equipment (see U.S. Pat. Nos. 5,057,095 and 5,664,582). The problem with this solution is that both the marker tags and the scanning equipment are expensive and do not necessarily work well in an operating room environment. As acknowledged in the '582 patent, the scanner must be essentially parallel to the marker tag inside a wadded up sponge. If the marker tag is bent or folded, a signal from the tag may be difficult to identify. In addition, the scanning equipment may give false counts if the operating room contains objects, other than the marker, that also generate or respond to magnetic energy.

Many other problems and disadvantages of the prior art will become apparent to one skilled in the art after comparing such prior art with the present invention as described herein.

SUMMARY OF THE INVENTION

The apparatus and method provided employ a "radiopaque" object to count and account for surgical sponges in an operating room. The term "radiopaque" refers to an object that is detectable by a scanning device using an x-ray or other penetrating wave or particle such as neutron beams or gamma rays, and infrared, near-infrared, laser, electromagnetic or radio waves. Within the context of the claimed subject matter, a "surgical sponge" is any device or material used in human or animal surgery for the purpose of absorbing blood or other fluids, or for packing off, containing, or isolating bodily structures within a surgical field.

A radiopaque object is embedded in each surgical sponge so that a scanning device can detect and count a large number of the sponges within a container designed to eliminate the need for contact by humans with the sponges. In this manner, a surgical team can insure that no surgical sponge is left in a patient without performing the messy and time-consuming job of individually counting sponges as they are entered and removed from the surgical site.

The claimed subject matter includes specially designed surgical sponges for use in the scanning device. Also included in the claimed subject matter is the use of radiopaque objects of differing sizes and/or types embedded in surgical sponges of differing sizes and/or types. For example, a large sponge may contain a large object and a small sponge may contain a small object so that the scanning device can distinguish and count multiple sizes and types of sponges. In one embodiment of the invention, the scanning device also weighs discarded surgical sponges so that a calculation can be made of the sponges' retained fluids, i.e. patient fluid loss.

Other systems, methods, features and advantages of the invention will be or will become apparent to one with skill in the art upon examination of the following figures, which are not necessarily drawn to scale, and detailed description. It is intended that all such additional systems, methods, features and advantages be included within this description, be within the scope of the invention, and be protected by the accompanying claims.

BRIEF DESCRIPTION OF THE FIGURES

While various embodiments of the invention have been described, it will be apparent to those of ordinary skill in the art that many more embodiments and implementations are possible that are within the scope of this invention.

DETAILED DESCRIPTION OF THE FIGURES

Although described with particular reference to a system for tracking surgical supplies within an operating room, the surgical supply tracking system (SSTS) of the disclosed subject matter can be implemented in any system in which it is desirable to count and/or track objects with a minimum of handling and a very high degree of accuracy.

Selected portions of the SSTS can be implemented in software, hardware, or a combination of hardware and software. Hardware portions of the invention can be implemented using specialized hardware logic. Software portions can be stored in a memory and executed by a suitable computing system such as a microprocessor or a personal computer (PC). Furthermore, software of the SSTS, which comprises an ordered listing of executable instructions for implementing logical functions, can be embodied in any computer-readable medium for use by or in connection with the computing system.

Figure 1:
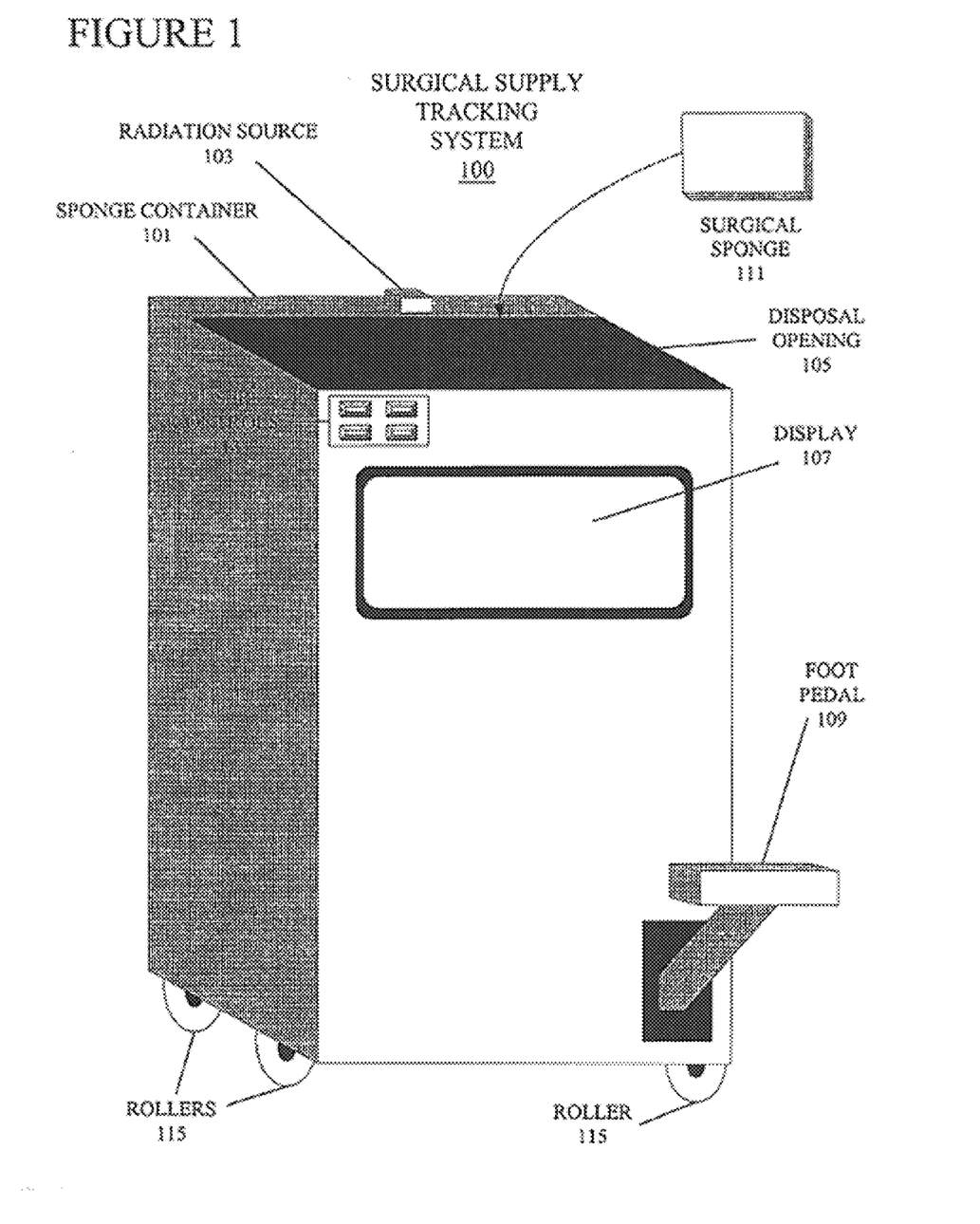
FIG. 1 is an exemplary surgical supply tracking system (SSTS) employing the techniques of the claimed subject matter.

Turning now to the figures, FIG. 1 illustrates an exemplary SSTS 100 for use in an operating room. A sponge container 101 includes a disposal opening 105 through which surgical sponges, such as a surgical sponge 111, are placed after use. For the purposes of this disclosure, a "surgical sponge" is any device or material used in either human or animal surgery for the purpose of absorbing blood or fluids, or for packing off, containing, or isolating bodily structures within a surgical field. The sponge container 101 includes rollers 115 to facilitate its movement within and outside the operating room. By pressing a foot pedal 109, a user of the SSTS 100 opens a door (not shown) in the disposal opening 105 so that the used surgical sponge 111 can be placed into the sponge container 101. In addition, the pressing of the foot pedal 109 causes hardware and/or software logic (not shown) in the SSTS 100 to activate a radiation source 103. The hardware and/or software logic, with input from a sensor (not shown), then calculates the number of sponges in the sponge container 101. Once the hardware and/or software logic has calculated the number of sponges in the sponge container 101, this number is displayed on a display 107. It should be apparent to those with skill in the electronic arts that the hardware and/or software logic of the SSTS 100 can be implemented in a number of ways, including, but not limited to, specialized circuits incorporating both hardware and software components.

The sponge container 101 also includes a clear plastic covering (not shown) such as a plastic bag or a form-fitted covering that fits into the disposal opening 105, thus containing the surgical sponges 111, and drapes over the outside of the container 101 in order to keep fluids from the surgical sponges 111 from contaminating the surface of the container 101 and its components. In addition to the number of sponges in the container 101, the display 107 may also display a calculation of the weight of the contained sponges so that operating room personnel can determine patient fluid loss. A set of user controls 113 are employed to turn the SSTS 100 on or off, initiate the display 107 and calibrate the sensors. In alternative embodiments of the SSTS 100, the calculation of the sponges in the container 101 and the display of this number may also be initiated by the user controls 113 rather than, or in addition to, the depression of the foot pedal 109.

Figure 2:
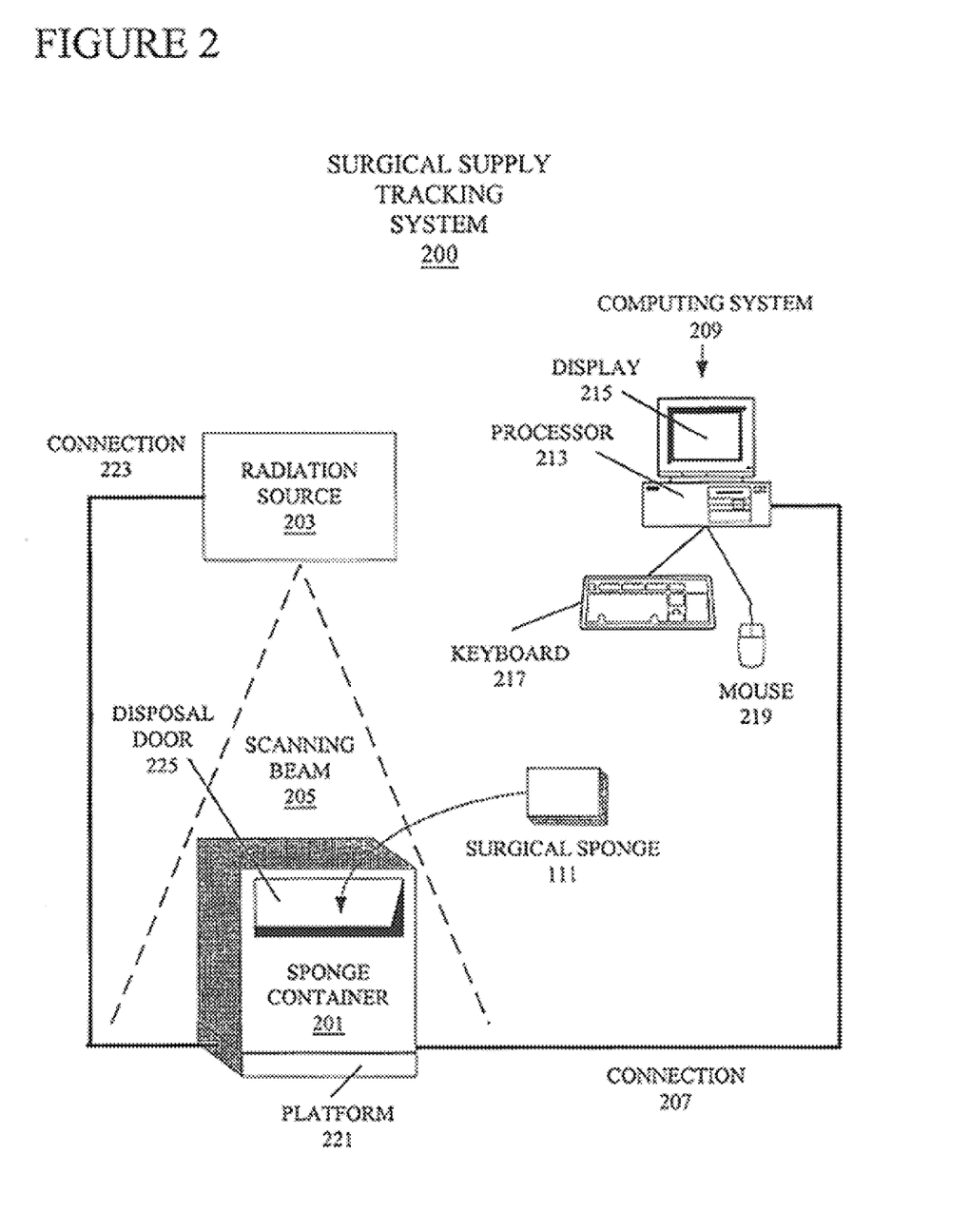
FIG. 2 is an exemplary PC-based SSTS employing the techniques of the claimed subject matter.

FIG. 2 illustrates an exemplary PC-based SSTS 200 employing the techniques of the claimed subject matter. The SSTS 200 includes a sponge container 201 in which surgical sponges, such as the surgical sponge 111 (FIG. 1), can be disposed following the sponge's 111 use in a surgical procedure. The container 201 is positioned on a platform 221 that is connected via a connection 223 to a radiation source 203, which is similar to the radiation source 103 (FIG. 1). The platform may also include a weight sensor (not shown) for measuring the weight of the container 201 and its contents. The platform 221 is also connected via a connection 207 to a computing system 209. The connections 223 and 207 may be hard-wired, wireless or network connections. In this example, the computing system 209 includes a processor 213, a display 215, a keyboard 217 and a mouse 219. The exact configuration of the computing system 209 is not critical to the spirit of the invention. For example, all or portions of the computing system 209 may be incorporated into the platform 221 in order to provide a compact and integrated system with fewer discrete pieces than the illustrated system 200.

The radiation source 203 emits a scanning beam 205 that enables detectors (not shown) in the platform to detect a small radiopaque object 301 (see FIGS. 3–7) in each sponge 111 in the container 201. The term "radiopaque" means the object 301 is able to obscure or block some type of scanning beam 205 such as x-ray or other penetrating wave or particle such as neutron beams, gamma rays, infrared, near-infrared, laser, electromagnetic waves or radio waves. The specific type of scanning beam 205 is not critical to the spirit of the inventions other than that the detectors in the platform 201 must be able to detect the scanning beam 205 with sufficient resolution to count each radiopaque object 301 in each sponge 111 in the container 101. As with the computing system 209, the radiation source 203 and the platform may be integrated into a single device, in which case the SSTS 200 would look more like the SSTS 100 (FIG. 1).

Figure 3:
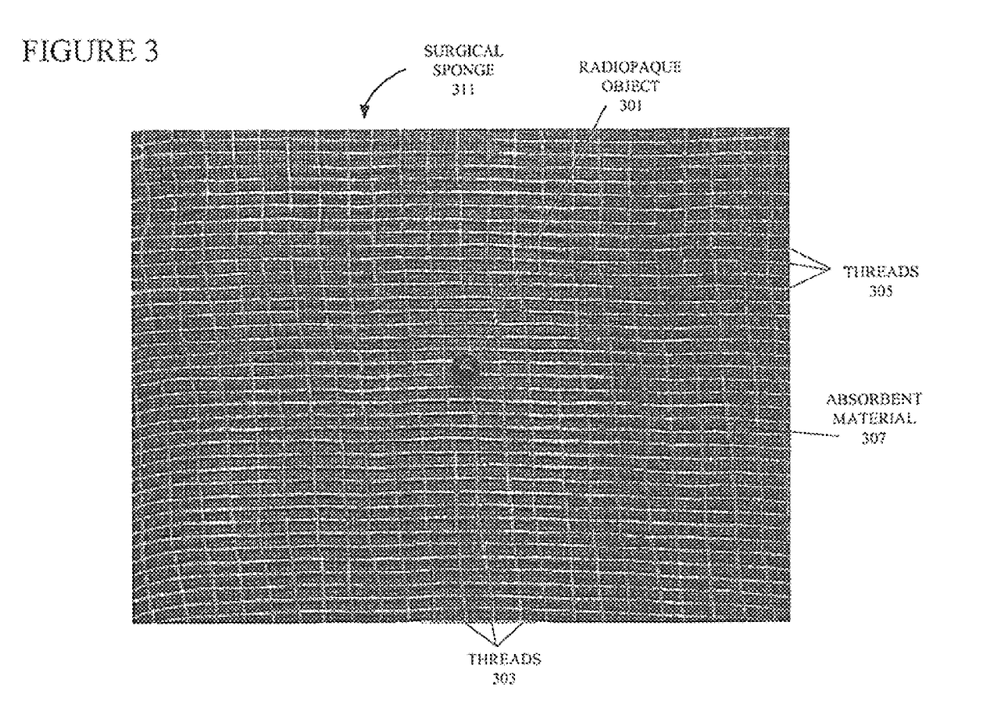
FIG. 3 is an illustration of a surgical sponge in relation to a radiopaque object according to the claimed subject matter.

FIG. 3 is an illustration of a surgical sponge 311 (FIG. 1) in relation to a radiopaque object 301. The surgical sponge 311 is one embodiment of the surgical sponge 111 (FIGS. 1 and 2). The surgical sponge 311 is comprised of an absorbent material 307 contained within vertical threads 303 and horizontal threads 305. Other examples of suitable surgical sponges include foam sponges or other sponges made of non-woven, non-knitted or non-fabric material. The surgical sponge 311, except for the radiopaque object 301, should be familiar to those with experience with surgery and the equipment employed in surgery. Although not necessarily drawn to scale, the radiopaque object 301 is small in relation to the surgical sponge 311. Typically, the radiopaque object 301 is less than one (1) centimeter wide in any direction. Although, the radiopaque object 301, illustrated in FIG. 3, is a metal sphere there can be different types of radiopaque objects; i.e., many different shapes and materials can be employed. For example, the radiopaque object 301 may be cylindrical, cubic, rectangular, triangular or some other polygon, either regularly or irregularly shaped. The radiopaque object 301 may also be some other shape such as a hexagonal nut, either with or without a hole in the middle. Different types of radiopaque objects can be used to indicate different types or sizes of surgical sponges. In addition, the radiopaque object may be something other than metal. For example, the object 301 may be barium sulfate encased in a non-water-soluble material such as plastic, latex, rubber, silicone or silastic, or even encased in a tightly woven fabric.

Figure 4:
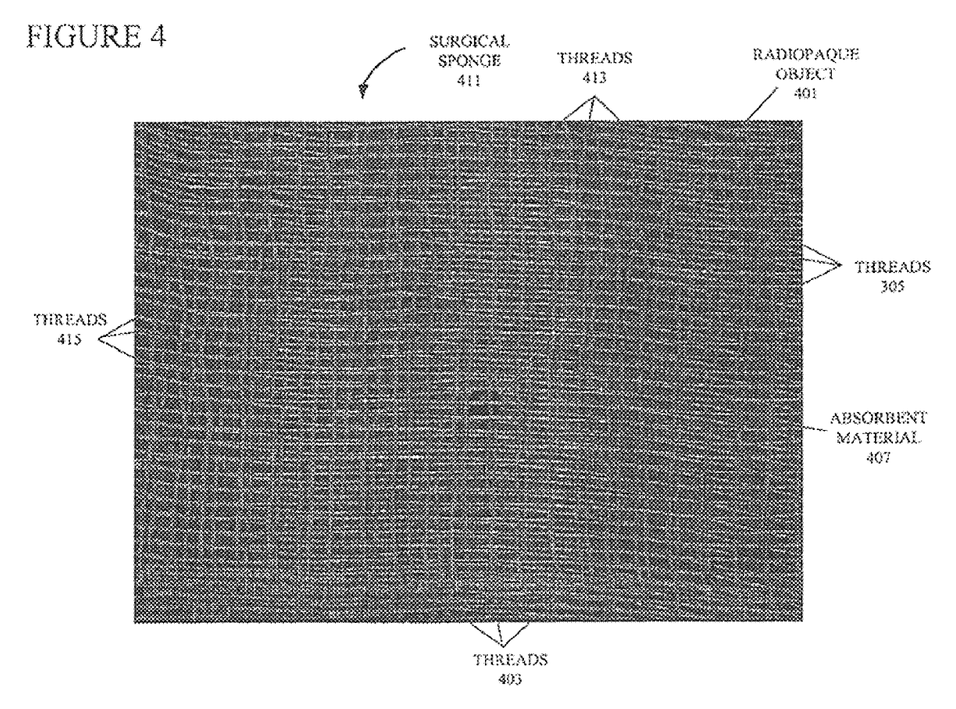
FIG. 4 is an illustration of an exemplary surgical sponge in which the radiopaque object is woven or glued into the surgical sponge.
Figure 5:
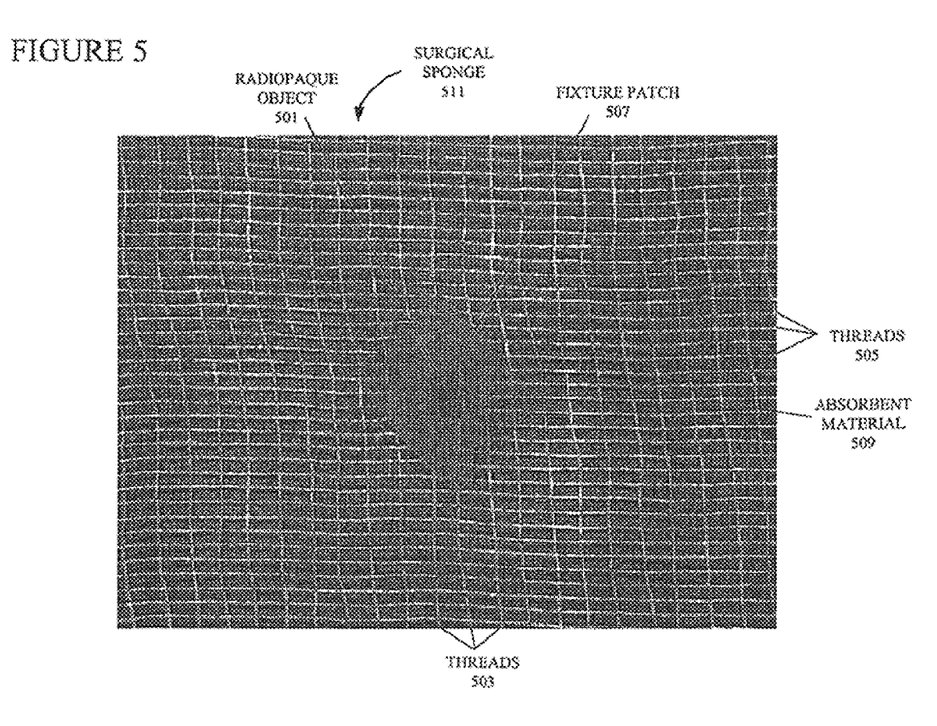
FIG. 5 is an illustration of an exemplary surgical sponge in which the radiopaque object is affixed to the surgical sponge by means of a fixture patch.
Figure 6:
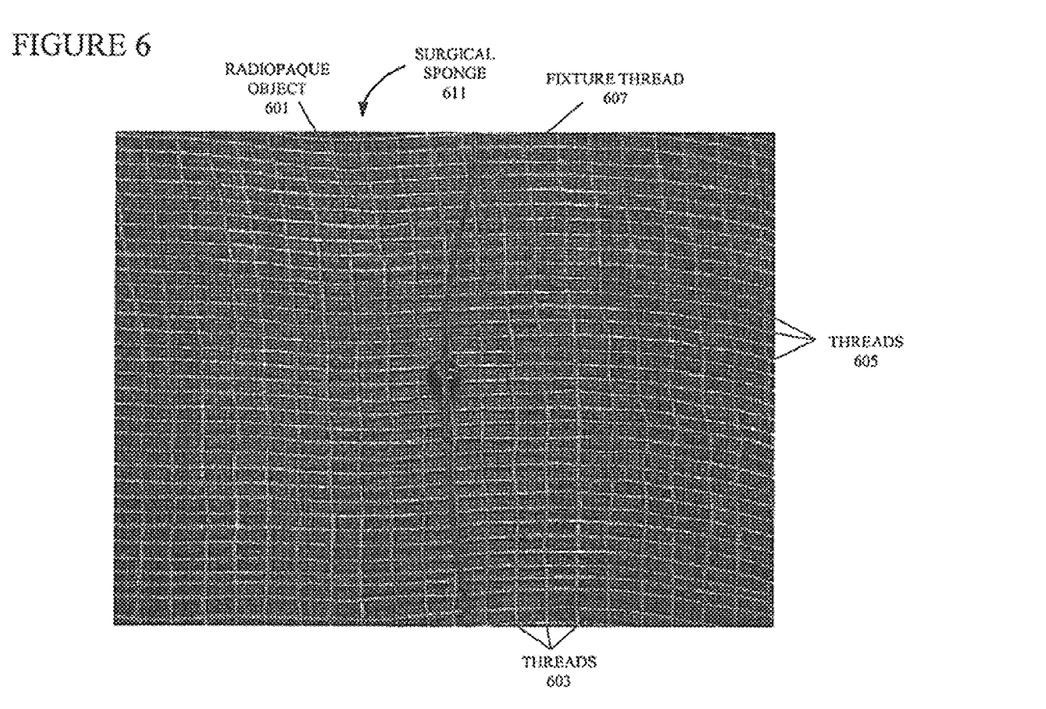
FIG. 6 is an illustration of an exemplary surgical sponge in which the radiopaque object is affixed to the surgical sponge by means of a fixture thread.
Figure 7:
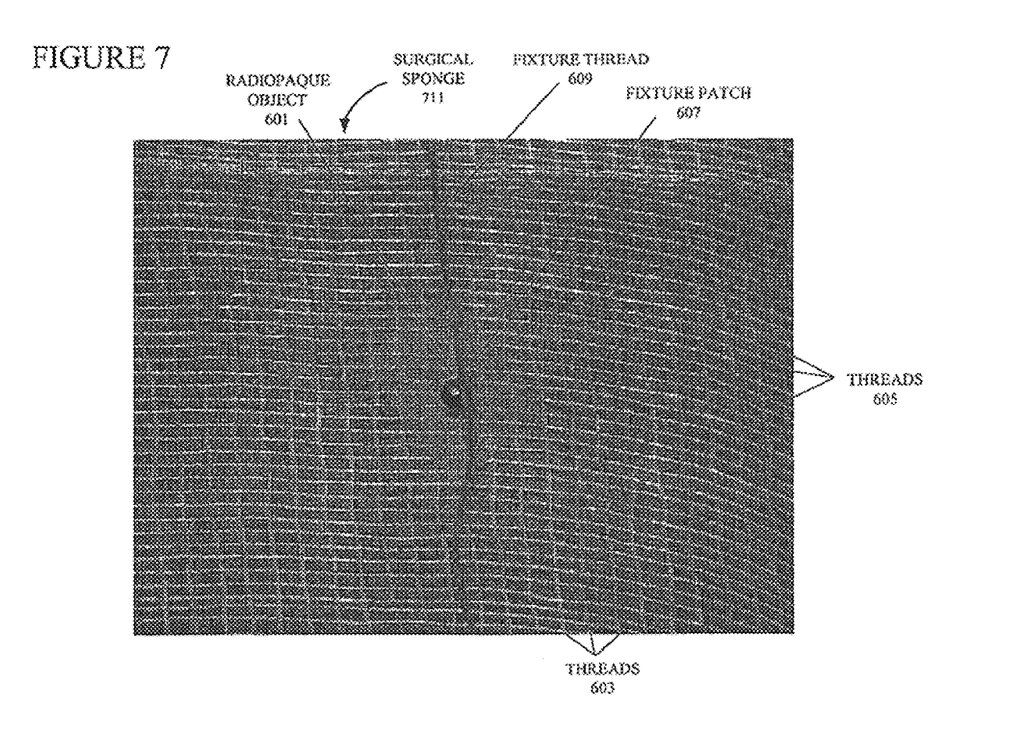
FIG. 7 is an illustration of an exemplary surgical sponge in which the radiopaque object is affixed to the surgical sponge by means of both a fixture patch and a fixture thread.

FIGS. 4–7 show alternative methods of affixing a radiopaque object, such as the radiopaque object 301, to a surgical sponge, such as surgical sponges 111 and 311. FIG. 4 is an illustration of an exemplary surgical sponge 411 with a radiopaque object 401 woven or glued into the surgical sponge 411. In other words, the radiopaque object 401 is held between vertical threads 403 and horizontal threads 405 by means of a second layer of vertical threads 413 and a second layer of horizontal threads 415 and/or glued into the surgical sponge 411. FIG. 5 is an illustration of an exemplary surgical sponge 511 with a radiopaque object 501 affixed by means of a fixture patch 507. The fixture patch 507 is a piece of latex, tape or fabric mesh that firmly attaches by means of sewing, gluing or weaving to the radiopaque object 501 and either or both of threads 503 and 505 and absorbent material 509. FIG. 6 is an illustration of an exemplary surgical sponge 611 with a radiopaque object 601 affixed by means of a fixture thread 607. The fixture thread 607 can be either tied to, threaded through or clamped by the radiopaque object 601 and then woven into vertical and horizontal threads 603 and 605. FIG. 7 is an illustration of an exemplary surgical sponge 711 with a radiopaque object 701 affixed by means of both a fixture patch 707, similar to the fixture patch 507 (FIG. 5) and a fixture thread 709, similar to the fixture thread 607 (FIG. 6).

Figure 8:
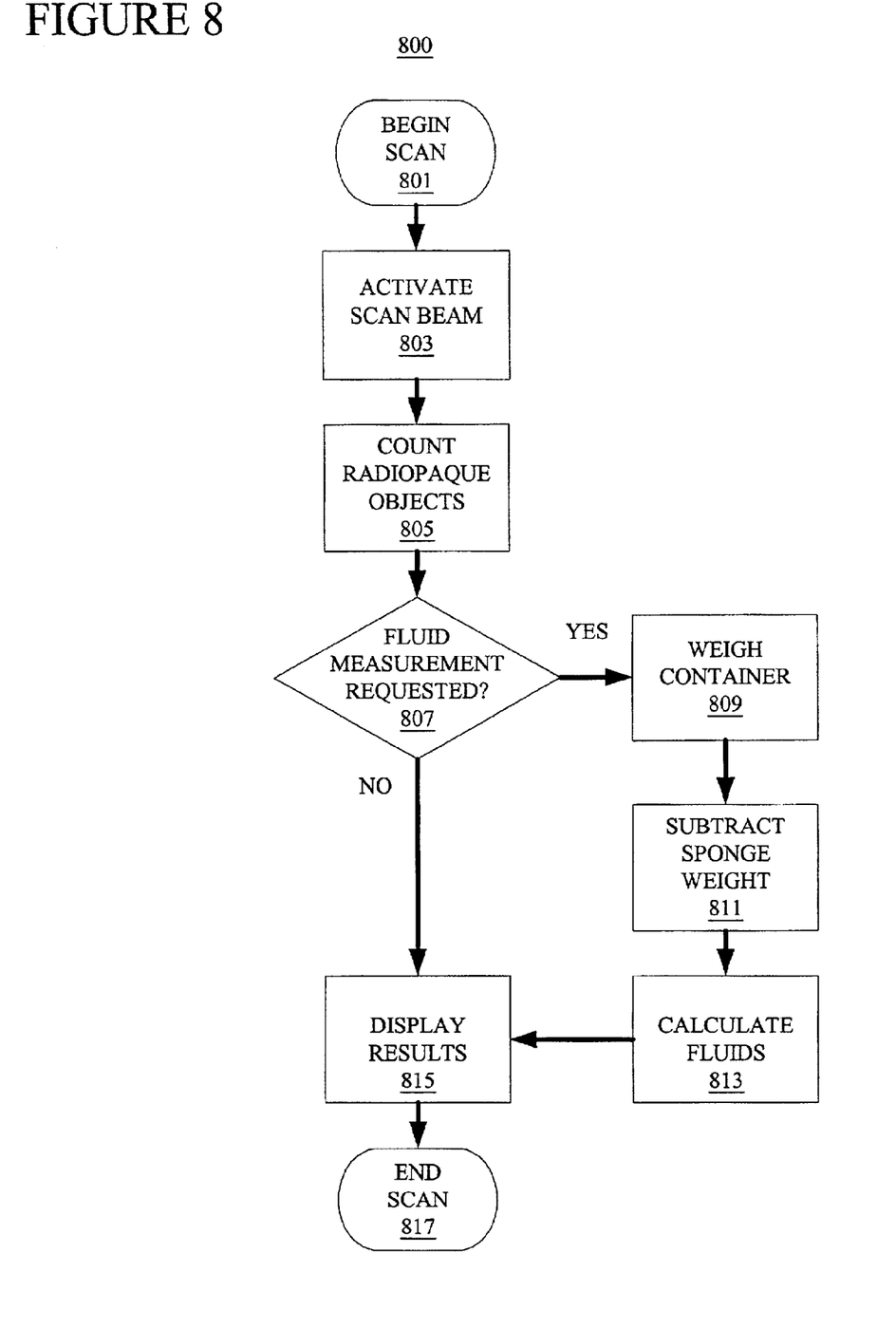
FIG. 8 is a flowchart that illustrates the processing performed by the SSTS.

FIG. 8 is a flowchart of a Count Sponge process 800 executed by either the SSTS 100 of FIG. 1 or the SSTS 200 of FIG. 2. The process 800 starts in a Begin Scan step 801 and proceeds immediately to an Activate Scan Beam step 803 in which the radiation source, such as the radiation source 103 (FIG. 1) or the radiation source 203 (FIG. 2) is activated. In the SSTS 100, the radiation source 103 is activated either by the foot pedal 109 or the user controls 113. In the SSTS 200, the radiation source 200 is activated by the computing system 209, either in response to user input on the keyboard 217 or mouse 209 or in response to a timer (not shown) that periodically updates a sponge count produced by the SSTS 200 and displayed on the display 215. In another embodiment of the SSTS 200, the radiation source 203 may be activated in response to the weight sensor in the platform 221 so that information displayed on the display 215 is updated in real time. Control then proceeds to a Count Radiopaque Objects step 805.

In step 805, a sensor detects the number of radiopaque objects such as object 301 (FIG. 3) in the surgical sponges such as surgical sponge 111 in the container 201 by detecting the scanning beam generated by either radiation source 103 or 203. A signal from the sensor is transmitted to the logic (SSTS 100) or the computing system 209 via the connection 207 (SSTS 200), enabling the logic or computing system 209 to calculate the specific number of sponges in the container 101 or 201, respectively. In one embodiment of the invention, surgical sponges of differing sizes or types each contain a radiopaque object of a size or shape that corresponds to the different size sponges. Using the different sizes or shapes, the logic or computing system 209 processes the signal from the sensor to determine not only a count but a specific count for each of the different sizes or types of sponges.

Following step 805, process 800 proceeds to a Fluid Measurement Requested step 807 in which, using the SSTS 200 as an example, the SSTS 200 determines whether information on the collective weight of the sponges in the container 201 is requested. If a weight measurement is not requested, then control proceeds to a Display Results step 815, in which the specific number of sponges calculated in step 805 is displayed on the display 215. In an alternative embodiment, rather than using the display 215, the number may simply be rendered in a display device such as a light emitting diode (LED) device on the platform 221 itself. Of course, if the SSTS 200 does not include a weight sensor in the platform 221, control proceeds directly from step 805 to step 815. If in step 807, process 800 determines that a fluid measurement step is required or requested, then control proceeds to a Weigh Container step 709, in which a weight sensor in the platform sends a signal representing the weight of the container 201 and its contents via the connection 207 to the computing system 209. Control then proceeds to a Subtract Sponge Weight step 811 in which the computing system 209 employs the weight signal, in conjunction with the count signal, to calculate a tare weight for the container 201 and its contents. Control then proceeds to a Calculate Fluids step 813 in which the computing system 209 determines, based upon the tare and the weight signal from the platform 201, the amount of fluids that have been absorbed by the sponges in the container 201. Control then proceeds to the Display Results step 815 in which both the sponge count and the fluid weight is displayed on the display 215 or other display device, such as the display 107 in the case of the SSTS 100. Following step 815, control proceeds to an End Scan step 817 in which processing is complete. Of course, as explained above, process 800 may execute periodically or be initiated by a user.

While various embodiments of the application have been described, it will be apparent to those of ordinary skill in the art that many more embodiments and implementations are possible that are within the scope of this invention. Accordingly, the invention is not to be restricted except in light of the attached claims and their equivalents. claims

I claim:

1. A surgical supply tracking system, comprising:
   a plurality of surgical sponges, each sponge comprising:
      a passive, radiographically detectable object securely fixed to the sponge, wherein the radiographically detectable object appears substantially the same shape when viewed from different angles;
   a scanning device for detecting each radiographically detectable object corresponding to each surgical sponge of the plurality of surgical sponges;
   a sponge counter coupled to the scanning device, comprising:
      a processor;
      a display;
      a memory;
      logic stored on the memory and executed on the processor for counting each radiographically detectable object; and
      logic for displaying on the display a number corresponding to the number of counted radiographically detectable objects.

2. The surgical supply tracking system of claim 1, further comprising a container for containing each particular surgical sponge after the particular surgical sponge has been removed from the surgical field.

3. The surgical supply tracking system of claim 2, further comprising a measurement device coupled to the container for weighing the surgical sponges in the container.

4. The surgical supply tracking system of claim 3, wherein the measurement device is coupled to the computing device and the computing device further comprises:
   logic for calculating and displaying an estimated amount of fluids contained in the surgical sponges in the container, the amount based upon a difference between the weight of the counted sponges in the container and the weight of a same number of unused sponges.

5. The surgical supply tracking system of claim 1, wherein the plurality of surgical sponges includes sponges of at least two different types and the corresponding radiographically detectable objects include objects of at least two different types, the type of each particular radiographically detectable object corresponds to the type of the corresponding surgical sponge.

6. The surgical supply tracking system of claim 5, wherein the types of radiographically detectable objects are related to the size of the radiographically detectable objects.

7. The surgical supply tracking system of claim 1, wherein the radiographically detectable objects are spherical.

8. The surgical supply tracking system of claim 1, wherein the radiographically detectable objects are non-spherical.

9. The surgical supply tracking system of claim 1, wherein the radiographically detectable objects are metal.

10. The surgical supply tracking system of claim 1, wherein the radiographically detectable objects comprise a non-metallic radiopaque substance.

11. The surgical supply tracking system of claim 10, wherein the non metallic radiopaque substance is barium sulfate encased within a non-water-soluble material.

12. The surgical supply tracking system of claim 1, further comprising:
    a tightly woven fabric for encasing each radiographically detectable object and for attaching each radiographically detectable object to the corresponding surgical sponge.

13. The surgical supply tracking system of claim 1, further comprising:
    a fixture thread attached to each radiographically detectable object for affixing each radiographically detectable object to the corresponding surgical sponge.

14. The surgical supply tracking system of claim 1, wherein each radiographically detectable object comprises:
    an interior material; and
    a non-water soluble material surrounding the interior material.

15. A trackable, surgical sponge apparatus, comprising:
    a plurality of surgical sponges; and
    a passive, radiographically detectable object securely affixed to each surgical sponge of the plurality of surgical sponges, wherein each radiographically detectable object appears substantially the same shape when viewed from different angles.

16. The trackable, surgical sponge apparatus of claim 15, wherein the plurality of surgical sponges includes sponges of at least two different types and the corresponding radiographically detectable objects include objects of at least two different types, the type of each particular radiographically detectable object corresponds to the type of the corresponding surgical sponge.

17. The trackable, surgical sponge apparatus of claim 16, wherein the type of each radiographically detectable object is related to the size of each radiographically detectable object.

18. The trackable, surgical sponge apparatus of claim 15, wherein the radiographically detectable objects are spherical.

19. The trackable, surgical sponge apparatus of claim 15, wherein the radiographically detectable objects are non-spherical.

20. The trackable, surgical sponge apparatus of claim 15, wherein the radiographically detectable objects are metal.

21. The trackable, surgical sponge apparatus of claim 15, wherein the radiographically detectable objects comprise anon-metallic radiopaque substance.

22. The trackable, surgical sponge apparatus of claim 21, wherein the non-metallic radiopaque substance is barium sulfate encased within a non-water-soluble material.

23. A method of tracking and counting surgical sponges, comprising the steps of:
    affixing a plurality of radiopaque objects in a plurality of surgical sponges, wherein each surgical sponge has one (1) radiopaque object;
    scanning a container containing a number of the plurality of surgical sponges that have been employed in a surgical field;
    determining, based upon the number of radiopaque objects detected in the scanning step, the number of surgical sponges in the container; and
    displaying on a display device the number of surgical sponges in the container.

24. The method of claim 23,
    wherein the plurality of surgical sponges includes surgical sponges of at least two different sizes and the corresponding radiographically detectable objects include objects of at least two different sizes, the size of each particular radiographically detectable object corresponds to the size of the corresponding surgical sponge;
    wherein the determining step further determines the number of each size of surgical sponge based upon the size of the corresponding radiopaque objects; and wherein the displaying step displays the count of each size of surgical sponges.

25. The method of claim 23, further comprising the steps of:
calculating an amount of fluid contained in the surgical sponges in the container by subtracting a tare weigh from the weight of the container.

26. A surgical sponge, comprising:
a tightly-woven, absorbent fabric; and
a passive, radiographically detectable object securely fixed to the fabric, wherein the radiographically detectable object appears substantially the same size when viewed from different angles.

27. The surgical sponge of claim 26, wherein there are at least two different types of sponges and the corresponding radiographically detectable objects include objects of at least two different types, the type of each particular radiographically detectable object corresponds to the type of the corresponding surgical sponge.

28. The surgical sponge of claim 27, wherein the types of radiographically detectable objects are related to the size of the radiographically detectable objects.

29. The surgical sponge of claim 26, wherein the radiographically detectable objects are spherical.

30. The surgical sponge of claim 26, wherein the radiographically detectable objects are non-spherical.

31. The surgical sponge of claim 26, wherein the radiographically detectable objects are metal.

32. The surgical sponge of claim 26, wherein the radiographically detectable objects comprise a non-metallic radiopaque substance.

33. The surgical sponge of claim 32, wherein the non-metallic radiopaque substance is barium sulfate encased within a non-water-soluble material.

34. The surgical sponge of claim 26, further comprising:
a fixture thread attached to each radiographically detectable object for affixing each radiographically detectable object to the corresponding surgical sponge.

35. The surgical sponge of claim 26, wherein each radiographically detectable object comprises:
an interior material; and
a non-water soluble material surrounding the interior material.

* * * * *